United States Patent [19]

Arndt et al.

[11] Patent Number: 4,718,896

[45] Date of Patent: Jan. 12, 1988

[54] APPARATUS AND METHOD FOR CONTROLLING THE FLOW OF FLUID THROUGH AN ADMINISTRATION SET

[75] Inventors: Robert G. Arndt, Waukegan, Ill.; William Atkinson, Cincinnati, Ohio; Travis C. Carr, Sandy, Utah; Michael J. Haun, Kenosha, Wis.; Phillip Loeb, Palatine, Ill.; Stanley D'Souza, Cincinnati, Ohio

[73] Assignee: Abbott Laboratories, North Chicago, Ill.

[21] Appl. No.: 817,812

[22] Filed: Jan. 10, 1986

[51] Int. Cl.⁴ .......................... A61M 5/00; G01F 1/00
[52] U.S. Cl. .................................. 604/253; 73/861.41
[58] Field of Search .................. 604/246, 65, 67, 245, 604/247, 251, 253, 256, 250; 73/861.41; 188/DIG. 13

[56] References Cited

U.S. PATENT DOCUMENTS

| | | |
|---|---|---|
| 3,563,090 | 2/1971 | Deltour . |
| 3,596,515 | 8/1971 | Cramer . |
| 3,609,379 | 9/1979 | Hildebrandt . |
| 3,994,423 | 11/1976 | Burg . |
| 4,001,801 | 1/1977 | Maulet . |
| 4,111,198 | 9/1978 | Marx et al. . |
| 4,173,224 | 11/1979 | Marx et al. . |
| 4,314,484 | 2/1982 | Bowman . |
| 4,328,800 | 5/1982 | Marx et al. . |
| 4,432,761 | 2/1984 | Dawe ................................. 604/253 |
| 4,452,273 | 6/1984 | Hanzawa et al. ............... 604/253 X |
| 4,493,710 | 1/1985 | King et al. ....................... 604/253 X |
| 4,496,351 | 1/1985 | Hiliel et al. ..................... 604/253 X |
| 4,498,901 | 2/1985 | Finch ............................... 604/253 X |
| 4,533,350 | 8/1985 | Danby et al. ...................... 604/253 |

Primary Examiner—Stephen C. Pellegrino
Attorney, Agent, or Firm—Leydig, Voit & Mayer

[57] ABSTRACT

A flow controller is provided that detects intervals between successive drops and responds to detection of intervals which are too long by shutting down operation of the administration set if the abnormal flow causing the long interval cannot be corrected. In response to detection of abnormal flow which is not clearly a high flow condition and/or an empty container, the flow controller sequentially opens, closes, re-opens and again closes the clamp of the controller in an attempt to restore normal flow. If normal flow is restarted before the sequence is completed, the controller returns to normal control of the fluid flow. Otherwise, completion of the sequence results in a shutdown of the system and activation of an alarm. In keeping with the invention, indicia are provided in connection with the drop chambers of the administration sets which are sensed by sensing means mounted to the drop detector of the flow controller in order to indicate to the controller the size of the orifice in the drop chamber. In addition, a plurality of drop sensors are provided which cooperate to provide a reliable drop signal for angles approaching 30 degrees from vertical.

25 Claims, 17 Drawing Figures

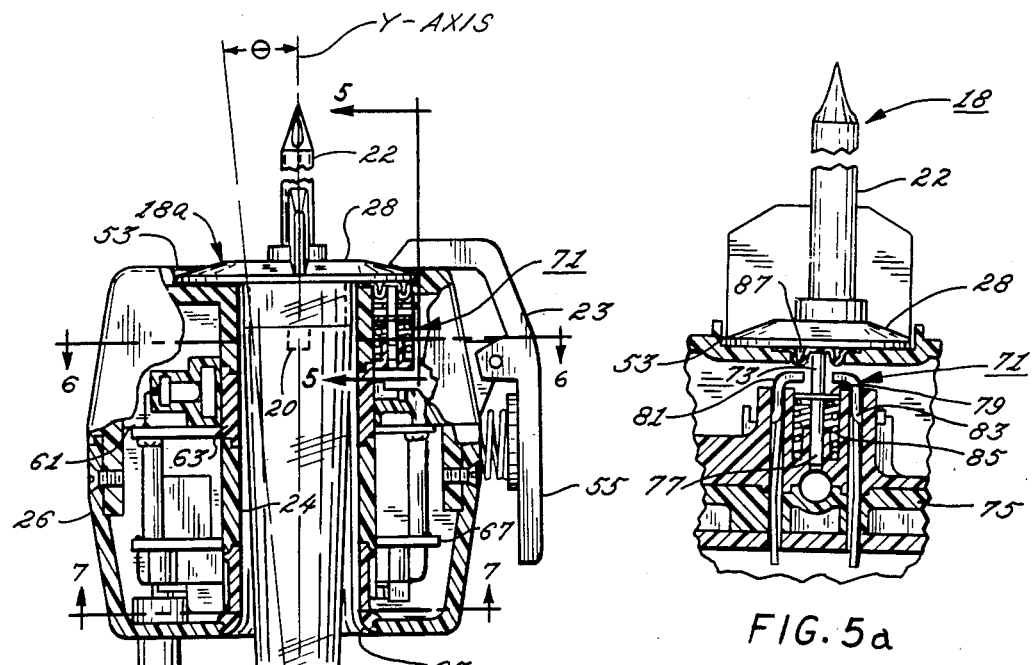
FIG. 4
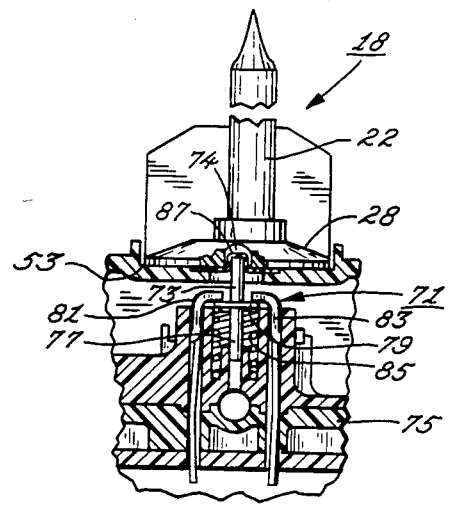
FIG. 5a
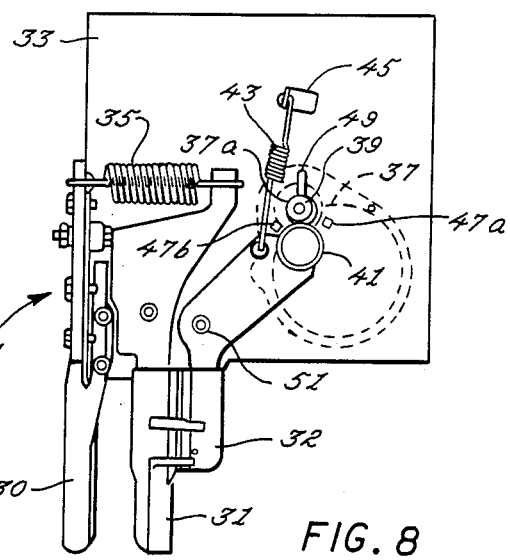
FIG. 5b
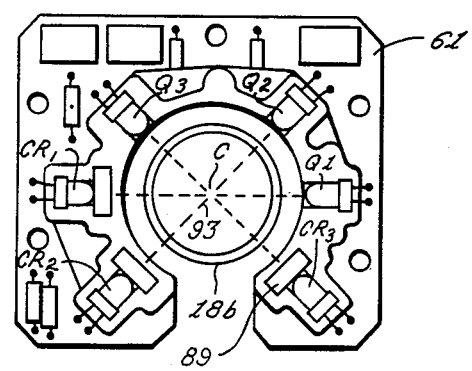
FIG. 6
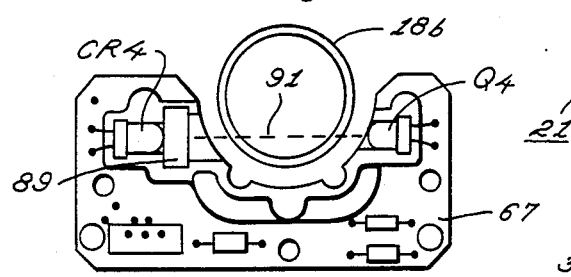
FIG. 7
FIG. 8

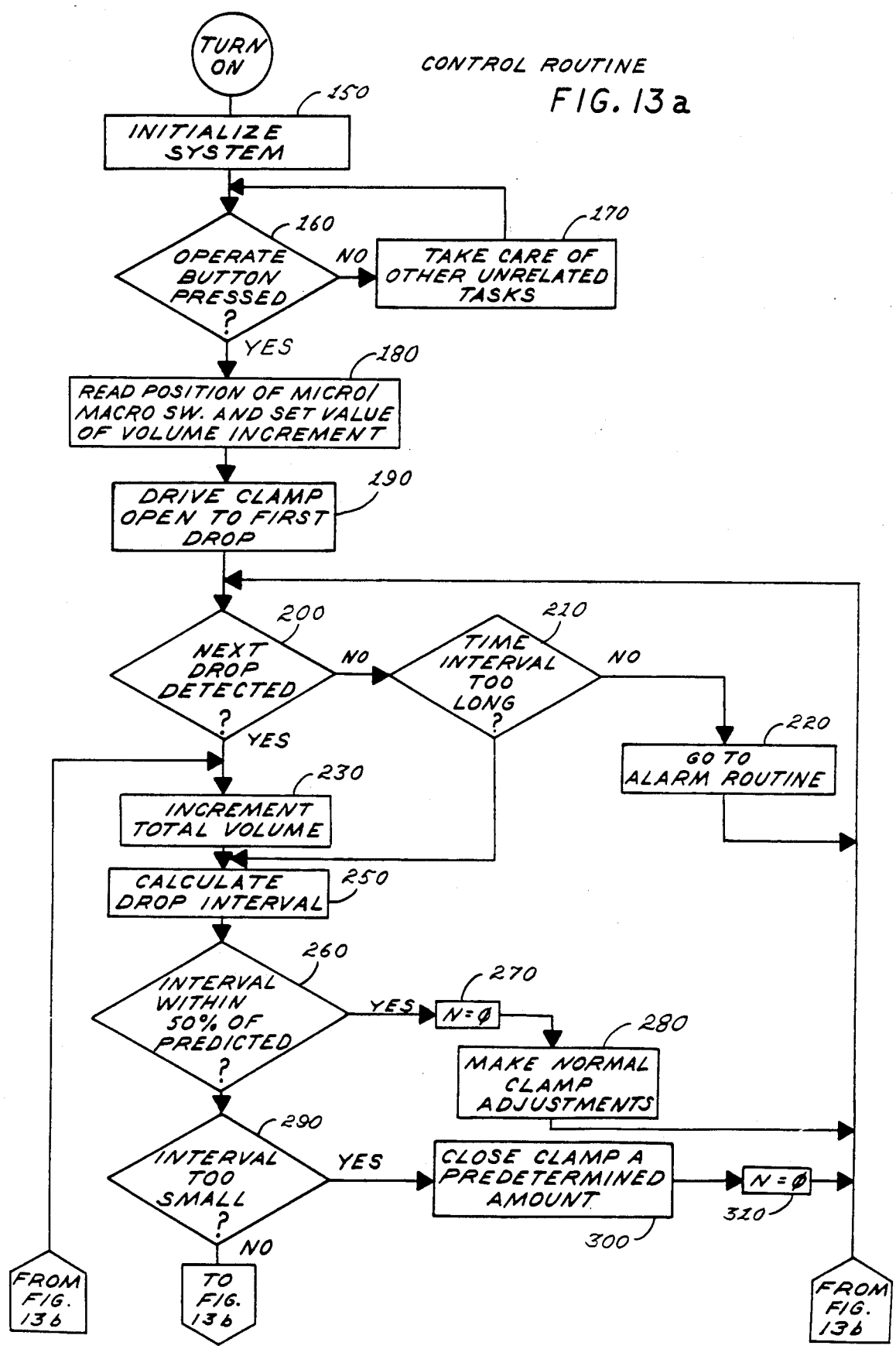

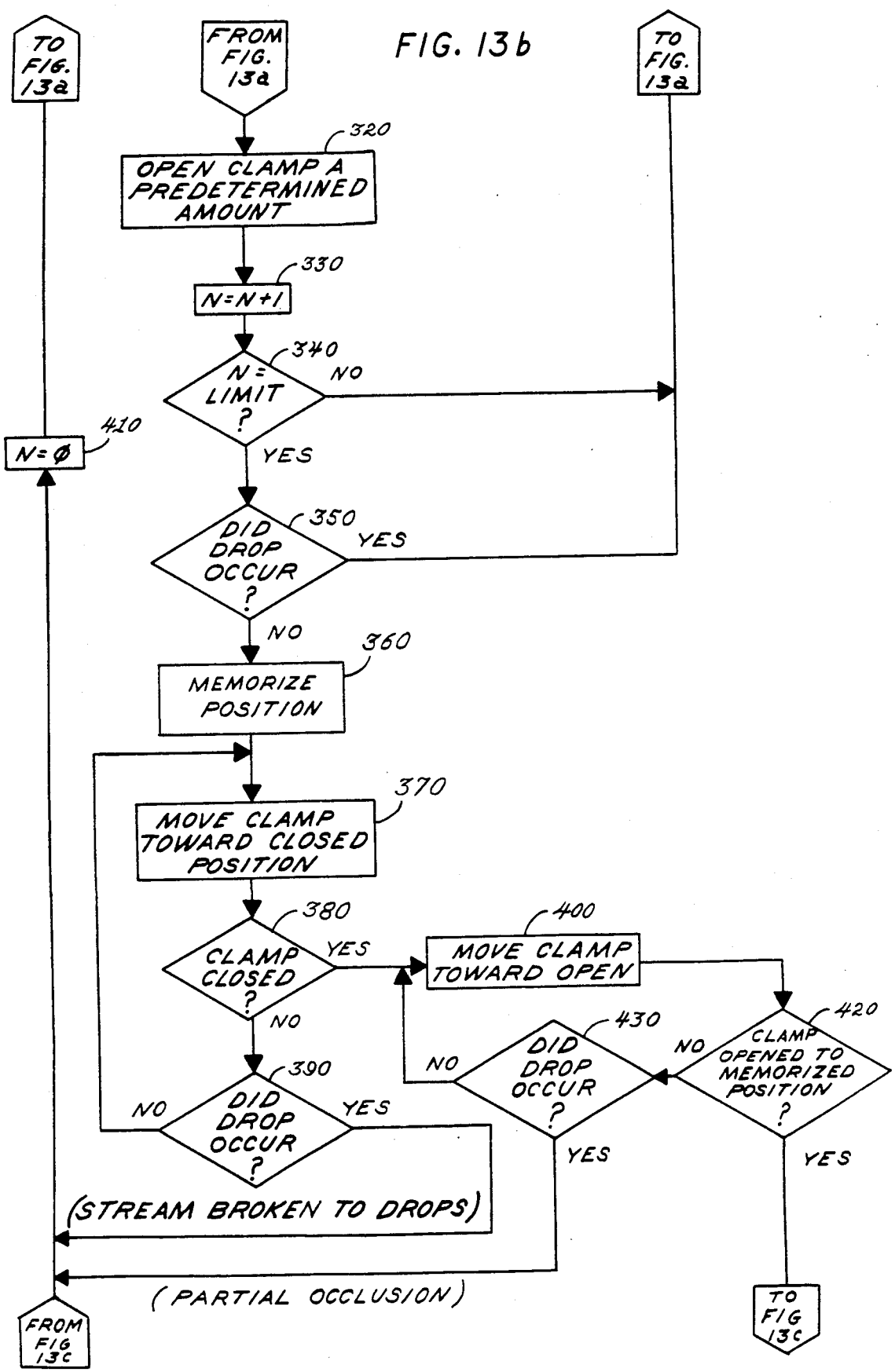

APPARATUS AND METHOD FOR CONTROLLING THE FLOW OF FLUID THROUGH AN ADMINISTRATION SET

FIELD OF THE INVENTION

The invention is generally directed to apparatus for controlling the flow of fluid through an administration set and, more particularly, to the detection and sizing of drops falling in a drop chamber of the administration set and the correction of abnormal flow in the set.

BACKGROUND

Many different types of administration sets are known for delivery of fluid to a patient. In a gravity-feed administration set, an elevated reservoir of the fluid to be administered provides a source for a downhill flow of fluid through the administration set. Resistance to the flow of the fluid is caused by a variety of natural sources; typically, most of the sources maintain a substantially constant resistance so that by adding an adjustable resistance to the flow, the operator of the administration set can control overall resistance to flow and thereby also control the rate of fluid flow to the patient.

In the past, to provide for a source of adjustable resistance it was common practice to place a clamp on the tubing leading the flow of the fluid from the reservoir to the patient. By manually varying the amount the clamp pinched the tubing, the resistance to flow was controlled. More recently, devices have been developed which automatically adjust the degree of pinching provided by the clamp in response to the sensing of the flow rate of the fluid. These devices are commonly called flow controllers, and they represent a significant improvement over manual adjustment of the clamp since the controller constantly monitors the flow and makes real-time adjustments to the flow resistance provided by the clamp if such adjustment is required. Real-time adjustment is a valuable feature since overall resistance to flow of the fluid may change during the course of delivery. For example, movement by the patient may cause the end of the catheter to slightly change its position in the vein of the patient. Such a change in position may cause an otherwise static source of flow resistance to suddenly change in value. Because of their ability to provide dynamic control of the resistance provided by the clamp, the flow controller compensates for changes in resistance to flow caused by movement of the patient and the like.

In addition to dynamic changes in the overall resistance to fluid flow in the administration set, changes may occur in the set which create fluid flow commonly referred to as abnormal flow. Abnormal flow is any flow rate which cannot be satisfactorily corrected by the normal real-time adjustment of the clamp of the flow controller. For example, dynamic changes in the flow characteristics of the administration set may result in the discrete drops falling in the drop chamber changing to a continuous stream of fluid. Such a continuous stream is particularly characteristic of a flow rate which is much too great for small-sized orifices in drop chambers. This condition is difficult to detect with the high degree of reliability required for safety considerations.

In contrast to streaming, abnormal flow may also be characterized by a stoppage of the flow. Such a stoppage of flow may be caused by a temporary and/or partial occlusion in the tubing of the administration set (e.g., the patient has rolled onto part of the tubing and, as a result, pinched off the flow), or it may be caused by an empty reservoir condition. The former cause is not immediately dangerous and the flow controller need not shut down operation of the administration set. But, the latter cause is immediately dangerous since air may be received by the administration set if operation is not quickly stopped.

To the best of applicants' knowledge, prior flow controllers have either failed to distinguish between abnormal conditions or have provided system responses for detection of abnormal conditions which are unsatisfactory, especially in the case of abnormal flow caused by temporary occlusions.

Another problem arises in connection with prior flow controllers because they require manual inputting of data to compensate for drop chambers of different sized orifices. As a result of this requirement, in order for the flow controller to accurately monitor total volume by counting drops formed by an orifice in the drop chamber, it has been necessary to rely upon the correct manual positioning of switches usually located on the front control panel of the controller for identifying the size of the orifice to the controller. Because the operator of the flow controller must manually position switches, the controller is only as reliable as the operator.

A further problem associated with prior flow controllers is the conventional drop detector associated with each controller is limited in the degree of tilting of the drop chamber which may occur before the detector is unable to detect a falling drop. Because a drop detector is typically mounted around the drop chamber and not directly secured to a stationary base, the detector and chamber may be vertically angled. In fact, slight angles of a freehanging drop chamber and detector are common. Therefore, it is important that the drop detector dependably detects drops at angles which may be reasonably expected to occur during the use of the flow controller.

SUMMARY OF THE INVENTION

It is the general object of the invention to provide a flow controller for gravity-feed administration sets which overcomes the foregoing problems.

It is a more particular object of the invention to provide a flow controller which is tolerant of temporary occlusions, yet it is capable of safely closing the path of flow for the administration set before an abnormally high flow condition becomes dangerous to the patient.

It is another particular object of the invention to provide a flow controller which is automatically calibrated during set up of the controller for recognizing the correct size of the orifice of the drop chamber.

It is yet another particular objective of the invention to provide a drop detector for the flow controller which reliably senses falling drops for tilt angles of the drop chamber which approach 30 degrees.

Briefly, the invention provides a flow controller which detects intervals between successive drops and responds to detection of intervals which are too long by shutting down operation of the administration set if the abnormal flow causing the long interval cannot be corrected. In response to detection of abnormal flow which is not clearly a high flow condition and/or an empty container, the flow controller sequentially opens, closes, re-opens and again closes the clamp of the controller in an attempt to restore normal flow. If normal flow is restarted before the sequence is completed, the controller returns to normal control of the fluid flow. Otherwise, completion of the sequence results in a shutdown of the system and activation of an alarm. In keeping with the invention, indicia are provided in connection with the drop chambers of the administration sets which are sensed by sensing means mounted to the drop detector of the flow controller in order to indicate to the controller the size of the orifice in the drop chamber. In addition, a plurality of drop sensors are provided which cooperate to provide a reliable drop signal for angles approaching 30 degrees from vertical.

BRIEF DESCRIPTION OF THE DRAWINGS

Other objects and advantages will become apparent with reference to the following detailed description when taken in conjunction with the drawings, in which:

FIG. 4 is a partial cross-sectional view of the drop detector of FIGS. 1 and 3 fitted to the drop chamber of the administration set and illustrating drop and fluid level detector apparatus positioned in the housing of the drop detector and a switch in accordance with the invention for automatically compensating for the size of the orifice in the chamber;

FIG. 5a is an enlarged cross-sectional view of the switch according to the invention taken along the line 5—5 in FIG. 4, showing the switch in a position indicative of an orifice of a first size;

FIG. 5b is the same view as illustrated in FIG. 5a, except the switch is shown in a position indicative of an orifice of a second size;

FIG. 6 is a plan view of a first circuit board substrate in the drop detector taken along the line 6—6 in FIG. 4 and illustrating a drop detector apparatus mounted on the board in accordance with the invention;

FIG. 7 is a plan view of a second circuit board substrate in the drop detector taken along the line 7—7 in FIG. 4 and illustrating a fluid level detector apparatus mounted on the board in accordance with the invention;

FIG. 8 is a plan view of a clamping mechanism of the flow controller, illustrating the supporting substrate within the controller and the mechanisms thereon for opening and closing the jaws of the clamp;

FIGS. 13a, 13b and 13c are flowchart diagrams of the control routine for the microprocessor-based circuitry of FIG. 12 which allows the flow controller to be responsive to the signals from the drop detector and level detector apparatus such that the controller responds to abnormal flow conditions in accordance with the invention.

Figure 1:
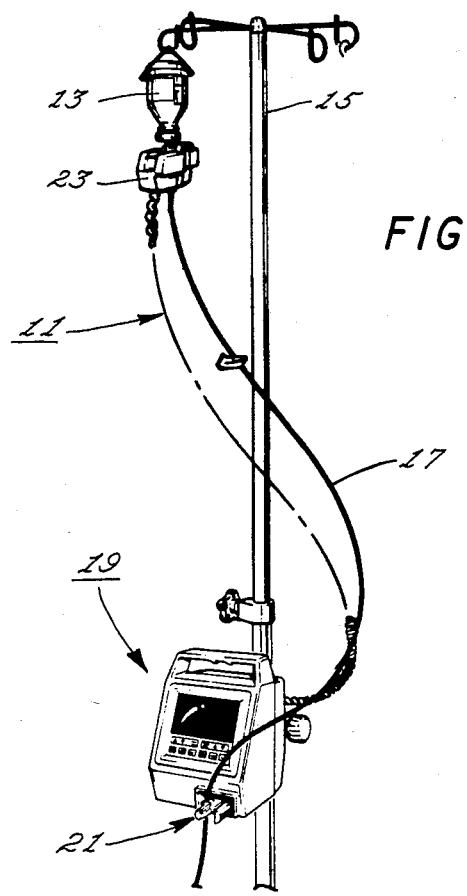
FIG. 1 is a perspective view of a flow controller coupled to an administration set for controlling the resistance to the gravity flow of fluid from an elevated container of the set.

While the invention is susceptible to various modifications and alternative forms, a specific embodiment has been shown by way of example in the drawings and will hereinafter be described in detail. It should be understood, however, that it is not intended to limit the invention to the particular form disclosed, but to the contrary, this invention is to cover all modifications, equivalents and alternatives falling within the spirit and scope of the invention as expressed in the appended claims.

DETAILED DESCRIPTION OF THE PREFERRED EMBODIMENT

Figure 3:
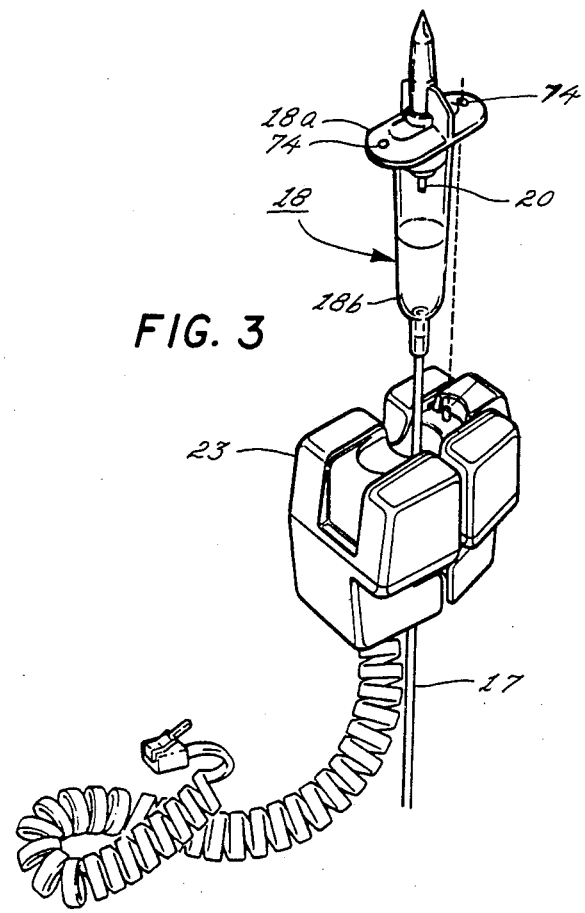
FIG. 3 is an exploded and enlarged perspective view of a drop detector of the flow controller in FIG. 1 and a drop chamber of the administration set according to the invention.
Figure 2:
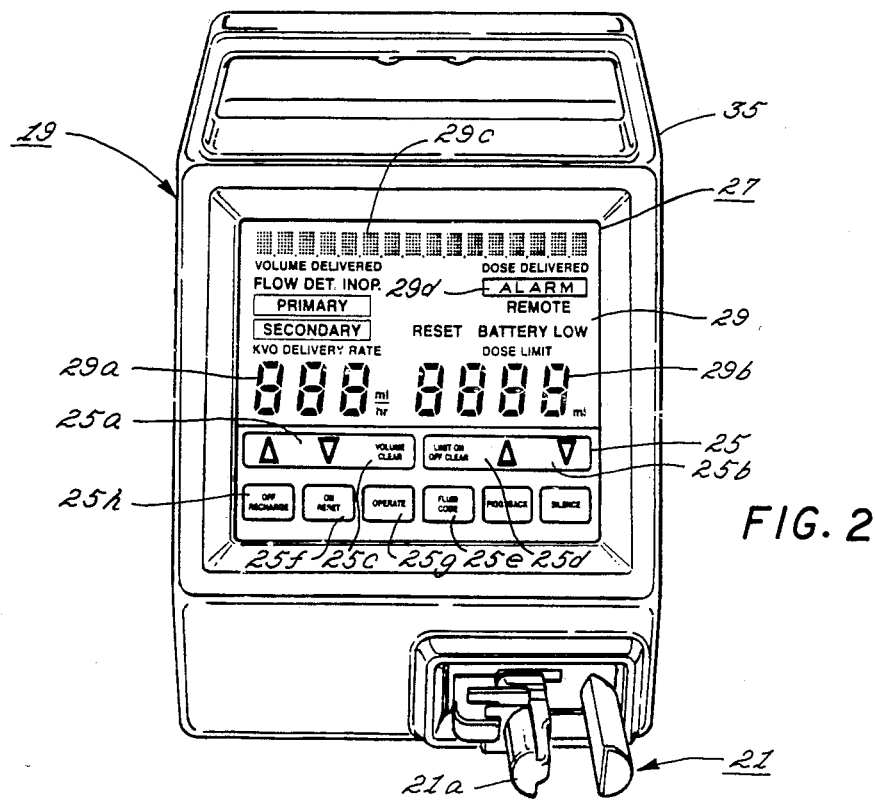
FIG. 2 is a front view of the main housing of the flow controller of FIG. 1, illustrating the front panel of the controller which includes touch switches for inputting data and a display for visualizing important operating parameters of the controller.

Turning to the drawings and referring first to FIGS. 1-3, an administration set 11 is illustrated which provides for gravity flow of fluids from an elevated reservoir held in a container 13 to a patient (not shown). The container 13 is positioned above the patient and supported by a stand 15. From the container 13, the fluid flows through a flexible tubing 17 and into a catheter (not shown) secured to the patient. The end of the tubing 17 leading the fluid from the container 13 includes a drop chamber 18 (shown in FIG. 3) having an upper portion 18a for mating the tubing with the container in a conventional manner. The upper portion 18a of the drop chamber 18 includes an orifice 20 and is connected the to a transparent plastic or glass lower portion 18b of the chamber wherein drops falling from the orifice are collected to form a small pool of fluid prior to entry of the fluid into the flexible tubing 17 of the administration set 11.

In a gravity-feed administration set such as shown in FIG. 1, the flow rate is typically controlled by a flow controller such as the LIFECARE 1050 Volumetric Controller, manufactured by Abbott Laboratories of North Chicago, Illinois. Such a flow controller provides for the automatic control of the resistance to fluid flow in the tubing of the administration set. By controlling the resistance to flow in the tubing, the flow controller is able to regulate the rate of fluid flow into the patient.

In the illustrated embodiment, a flow controller 19 receives a segment of the tubing 17 in an electromechanical clamping mechanism 21 which variably pinches the tubing and thereby provides a variable resistance to fluid flow in the tubing. Microprocessor circuitry within the flow controller 19 provides control signals for the electromechanical clamping mechanism 21 in response to flow signals received from a drop detector 23. In order to sense the flow of fluid through the tubing 17, the drop detector 23 is fitted about the drop chamber 18 for sensing the falling of drops into the lower portion 18b of the chamber.

By detecting each falling drop falling in the lower portion 18b of the drop chamber, the drop detector 23 provides information to the microprocessor circuitry of the flow controller 19 from which the actual flow rate can be determined. After comparing the actual flow rate with a predetermined desired flow rate, the microprocessor circuitry commands the clamping mechanism 21 to electromechanically adjust a pinch clamp 21a to reduce, increase or hold constant the degree of pinching of the tubing 17. If the microprocessor circuitry determines the actual flow rate requires adjustment, the degree of pinching of the tubing 17 by the clamping mechanism 21 and pinch clamp 21a is changed and, in response thereto, the resistance to fluid flow in the tubing is also changed, and the flow rate is adjusted accordingly.

Referring to FIG. 8 of the illustrated embodiment, the clamping mechanism 21 is composed of three arm segments 30, 31 and 32. The first arm segment 30 is rigidly secured to a substrate 33 within the housing 35 of the flow controller 19, whereas the second and third arm segments 31 and 32, respectively, are pivotally secured to the substrate. The tubing 17 is pinched by a clamping action provided by the second and third arm segments 31 and 32 acting as opposing jaws of the pinch clamp 21a. In order to place the tubing 17 into the jaws of the clamp 21a formed by segments 31 and 32, the user wraps his/her hand around the first and second arm segments 30 and 31, respectively, and draws the second arm segment away from the third by squeezing the first and second segments together. Because the first arm segment 30 is rigidly secured to the substrate, it acts as a reference surface for the user's hand in overcoming the biasing force provided by spring 35 which tends to close the arms 31 and 32 together.

In operation, the second arm segment 31 remains stationary while the position of the third arm segment 32 is controlled by the microprocessor circuitry of the flow controller 19 to adjust the degree of pinching of the tubing provided by the clamp 21a formed by the arms. To move the third arm segment 32, a stepper motor 37 is mounted to the substrate 33 along with the arm segments 30–32, and it includes an offset cam surface 39 (a stainless steel disk) which directly engages a cylindrical cam follower 41 mounted to one end of the third arm segment. A spring 43 connecting the third arm segment 32 to an anchor 45 on the substrate 33 biases the cam follower 41 against the offset cam 39. Because the axis of rotation of the cam 39 of the stepper motor 37 is offset from its geometric center, a typical S-shaped line is charted by a graph of the angle of rotation of the cam versus the distance from its axis of rotation to the point of contact with the cam follower. Rotation of the cam causes the third arm segment 32 to pivot about its pivot point 51 on the substrate 33, and is limited to less than a full rotation by a pair of limit stops 47a and 47b.

As explained more fully hereinafter, the offset cam 39 initially rotates against the cam follower 41 from a position where a reference pin 49 mounted to the cam 39 engages one of the pair of limit stops 47a and 47b and forces the third arm segment 32 to pivot and thereby open the clamp 21a until flow starts. From this initial position, the offset cam 39 is continuously adjusted by incremental movement of the stepper motor 37 until the desired flow rate is achieved. The offset cam 39 does not continuously turn while the controller 19 is in operation. Instead, it makes very small incremental movements about a position to compensate for system variables in order to hold the flow rate stable. When a shutdown of the system is demanded, the stepper motor 37 is pulsed to rotate the cam 39 a full rotation from one stop 47a or 47b to the other. By providing motor pulses for a full rotation of the cam 39, it is intended to guarantee that the reference pin 49 reaches one of the stops 47a or 47b, and the cam is fully closed.

The flow controller 19 includes a control panel 27 comprising a display 29 and a plurality of touchswitches 25. As illustrated in FIG. 2, the display 29 includes all the fixed messages provided by the aforementioned LIFECARE 1050 Controller. Any one or group of messages may be activated by the microprocessor circuitry of the controller 19.

The front panel FLUID CODE 25e switch allows selection of the appropriate fluid code for more accurate measurement of fluid flow based on fluid characteristics. In the LIFECARE 1050, there are three fluid code settings which reflect the fluid groups described below: code 1 is the setting for most aqueous solutions such as electrolytes, low sugar, dextran, mannitol and lipid solutions; code 2 is the setting for solutions such as TPN and high sugar solutions which tend to form smaller drops for a given orifice; and code 3 is the setting for solutions such as vitamin additives, enteral, urea and alcohol solutions which tend to form the smallest drops.

The three and four digit seven-segment displays 29a and 29b, respectively, are for displaying the desired delivery rate of the fluid and the total desired dosage, respectively. In order to set the desired delivery rate and dosage of a fluid, two pairs of up/down touchswitches 25a and 25b (identified by up and down arrows) are provided which each increment one of the seven-segment displays. In connection with the up/down touchswitches 25a and 25b for entering the desired delivery rate, a "VOLUME CLEAR" touchswitch 25c is included. For the up/down touchswitches 25b which increment dosage display, a "LIMIT ON/OFF CLEAR" 25d touchswitch is included.

In order to visualize the FLUID CODE 25e entered by the user, a variable message field 29c appears across the top of the display 29. It also serves to display other data such as actual volume delivered. Preferably, the variable message field 29c is composed of a series of dot matrices.

Pressing the "ON/RESET" touchswitch 25f on the control panel 27 applies power to the microprocessor circuitry and initializes the system software. Also, pressing the "ON/RESET" touchswitch 25f will reinitialize the circuitry and software after a shutdown of the system has occurred in response to an abnormal flow condition that could not be safely corrected. When such a shutdown does occur, an "ALARM" message 29d is activated on the display 29. In addition to the visual message, an audible alarm is also provided.

After the controller 19 has been turned on and initialized and all appropriate data has been entered by the user and after the administration set 11 has been prepared for initiation of fluid delivery, the user presses an "OPERATE" touchswitch 25g on the control panel 27 which starts the flow controller 19 in its task of controlling fluid flow. Inasmuch as an understanding of the functions of the other messages and touchswitches illustrated in FIG. 2 is not necessary to fully understand the invention, they will not be discussed except to note that they are under microprocessor control and are active only when required - the single exception to this being the "OFF/RECHARGE" touchswitch 25h.

As indicated above, the drop chamber 18 typically comprises an elongated, transparent and cylindrical lower portion 18b communicating to the tubing 17 and an upper portion 18a including an orifice 20. Referring to FIG. 4, the upper portion 18a also includes a spike 22 for insertion into the container 13. In a conventional manner, the spike 22 allows fluid to flow from the container 13 and into the orifice 20 where it forms drops that fall from the orifice into a pool of fluid held in the lower portion 18b of the drop chamber. A cylindrical bore 24 in the housing 26 of the drop detector 18 receives the lower portion 18b of the drop chamber. In the illustrated embodiment, the orifice 20 and spike 22 are integrated into a single piece (preferably plastic) having a shoulder section 28 whose shape fits into a recess 53 of complementary shape in the drop detector 23. In order to hold the drop chamber 18 in engagement with the drop detector 23, a clamp 55 rests over the shoulder 28 when it is fitted into the recess 53 as illustrated in FIG. 4.

The orifices 20 of drop chambers 18 may be of different types such that the size of the drops formed in the chamber are different for each type. Typically, drops are either micro or macro sized (i.e., 1/60th milliliters for a micro-drop and 1/15th milliliters for a macro-drop). In order for the flow rate to be determined by the sensing of drops from the drop detector 23, the flow controller 19 must associate a volume value for each drop. The volume of fluid contained in each drop is dependent upon the size of the orifice 20, the flow characteristics of the fluid and the rate of the drop formation. Conventionally, data has been entered into the flow controller 19 via the control panel 27 in order to establish the foregoing three parameters. For example, the general fluid drop characteristics are compensated for by the fluid code data entered by the FLUID CODE touchswitch 25e.

In order to position the lower portion 18b of the drop detector within the cylindrical bore 24, the recessed area 53 of the drop detector 23 associated with the bore 24 of the detector receives the upper portion 18a of the drop chamber 18. Because of the placement of the drop chamber 18 within the bore 24, circuitry associated with the drop detector 23 is able to detect drops falling in the chamber. Specifically, a substrate 61 supports drop detecting apparatus which provide a radiation link spanning the bore 24. Each falling drop perturbs the radiation link and thereby provides the apparatus with an indication of a drop. In order for the radiation link to cross the bore 24, the wall of the bore in the area of the apparatus is a transparent annular ring 63 made from clear plastic or glass. Annular ring 63 provides a wall section of the bore 24 which functions as a window for the drop detector or apparatus placed on the substrate 61 at a location along the longitudinal axis of the bore 24 (the Y-axis in FIG. 4) such that the radiation link passes through an area of the drop chamber in which a falling drop occurs. Located under the drop detecting apparatus on substrate 61 is a level detecting apparatus on substrate 67 for detecting the level of fluid pooled at the bottom of the drop chamber 18. To allow the radiation link for the level detecting apparatus to cross the bore 24 a transparent annular wall section 65 is provided in the bore. Although the drop and level detecting apparatus are preferably electromagnetic radiation devices creating optical links across the bore 24, they may also be other types of radiation devices such as sonic radiation devices.

In accordance with one important aspect of the invention, the drop chamber 18 includes indicium or indicia which represent the size of the orifice 20 of the chamber, and the drop detector 23 includes sensing means for detecting the indicia when the drop chamber is fitted into the bore 24 of the drop detector. In response to the indicia, the drop detector 23 provides the flow controller 19 with an electronic signal indicative of the size of the orifice 20 in the drop chamber 18. Accordingly, mating of the drop chamber 18 and the drop detector 23 automatically provides data to the controller 19 which is one of the parameters necessary to determine the size of the drops detected by the drop detector and thereby accurately control the rate of fluid flow.

Preferably, the indicia are located in an area of the lower surface of the shoulder 28 of the drop chamber 18 and the sensing means is in the recessed area 53 of the drop detector 23 which receives the shoulder of the drop chamber. In the illustrated embodiment of FIGS. 4 and 5a-b, the sensing means is a switch 71 housed inside the drop detector 23 and operatively coupled to a spring-loaded rod 73 protruding from the housing 26 at the area of the recess 53. For the structure of the area of the lower surface of the shoulder 28 which comprises the indicia, it is preferably either a solid flat surface which engages the spring-loaded rod 73 and presses it into the housing 26 as indicated in FIG. 5a or a holed area which receives the spring-loaded rod as indicated in FIG. 5b. In this preferred embodiment, by pressing the rod 73 into the housing 26, the switch 71 is placed in a first state (open contacts as shown in FIG. 5a) which is indicative of an orifice 20 of a first size. By allowing the switch 71 to stay in its quiescent state (closed contacts as shown in FIG. 5b), the drop chamber 18 is identified as having an orifice 20 of a second size.

Referring more specifically to FIGS. 5a and 5b, the construction of the switch 71 is supported on a substrate 75 mounted within the housing 26 of the drop detector 23. The spring-loaded rod 73 is retained in a bore 77 formed in the substrate so that it is free only to move along its longitudinal axis. Rigidly secured to the rod 73 is a metallic ring 79 which serves both as a stop for the axial movement of the rod and as a means to bridge the opposing contacts 81 and 83 of the switch 71.

In FIG. 5a, the switch 71 is shown in its open state since a flat, solid area on the underside of the shoulder 28 of the drop chamber 18 has pressed the rod 73 into the housing 26 of the drop detector 23. Upon removal of the drop chamber 18 or upon replacement of the drop chamber with a chamber having an orifice 20 of a different size (and therefore a hole 74 through the shoulder 28 as shown in FIG. 5b), a spring 85 which biases the rod 73 to protrude from the housing 26 will cause the metallic ring 79 to engage the opposing contacts 81 and 83, thereby closing the switch 71. In order to prevent moisture and dirt from entering the housing 26, an elastomeric material 87 covers the hole in the housing through which the rod 73 protrudes. Other types of complementary indicia and sensing means may be used in substitution for the switch 71 and flat/holed area of the shoulder 28 of the drop chamber 18. For example, magnets placed in the shoulders 28 of drop chambers 18 having orifices 20 of a first size may be detected by a Hall Effect device mounted inside the housing 26 of the drop detector 23.

FIGS. 6 and 7 show the preferable physical arrangement of the radiation emitters and detectors for detecting fluid drops and level, respectively. For drop detection, three pairs of radiation emitters and detectors (preferably, infrared photodiodes and phototransistors) are each positioned to form an optical link 93 (shown as a broken line in FIG. 6) passing through the center of the bottom portion 18b of the drop chamber when the chamber is inserted into the bore 24 of the drop detector 23. Each photodiode $CR_1$, $CR_2$ and $CR_3$ has associated with it an infrared filter 89.

In order to detect the level of fluid pooled in the bottom of the drop chamber 18, a photodiode $CR_4$ mounted on the substrate 67 is optically linked to a phototransistor $Q_4$ also mounted on the substrate. The sensor pair is mounted to the substrate 67 so as to provide an optical link 91 which passes through the drop chamber 18, when it is joined to the drop detector 23, at an area of the chamber which normally is filled with fluid. Therefore, the infrared light, is normally deflected and the optical link is broken. When the pool of fluid in the drop chamber falls below the level of the sensor pair on the substrate 67, the container 13 is probably empty; therefore, the microprocessor-based circuitry of the flow controller 19 is programmed to react accordingly as explained more fully hereinafter.

Because the optical links 91 and 93 are generated by pairs of sensors mounted to substrate 67 and 61, respectively, each link is approximately orthogonal to the longitudinal axis (Y-AXIS in FIG. 4) of the drop chamber 18 and approximately coplanar to a reference plane defined by the surface of either substrate 61 or 67.

In accordance with another important aspect of the invention, two of the pairs of sensors in the drop detector apparatus are positioned on the substrate 61 at 90° with respect to one another, and the third pair is positioned between the first and second pairs such that its optical link is angled at 45° with respect to the first two pairs. The optical links 93 of the pairs of photodiodes and phototransistors are directed to cross approximately at the cross-sectional center C of the drop detector 18. A falling drop produces refraction, reflection and/or blockage of the optical links which create a biphasic signal response in the phototransistors as explained hereinafter. It has been established from empirical evidence, that the foregoing arrangement of sensor pairs provides a superior drop detection ability. Specifically, it has been determined that drops can be reliably detected for tilt angles $\theta$ (FIG. 4) of the drop chamber 18 which approach 30°.

Figure 9:
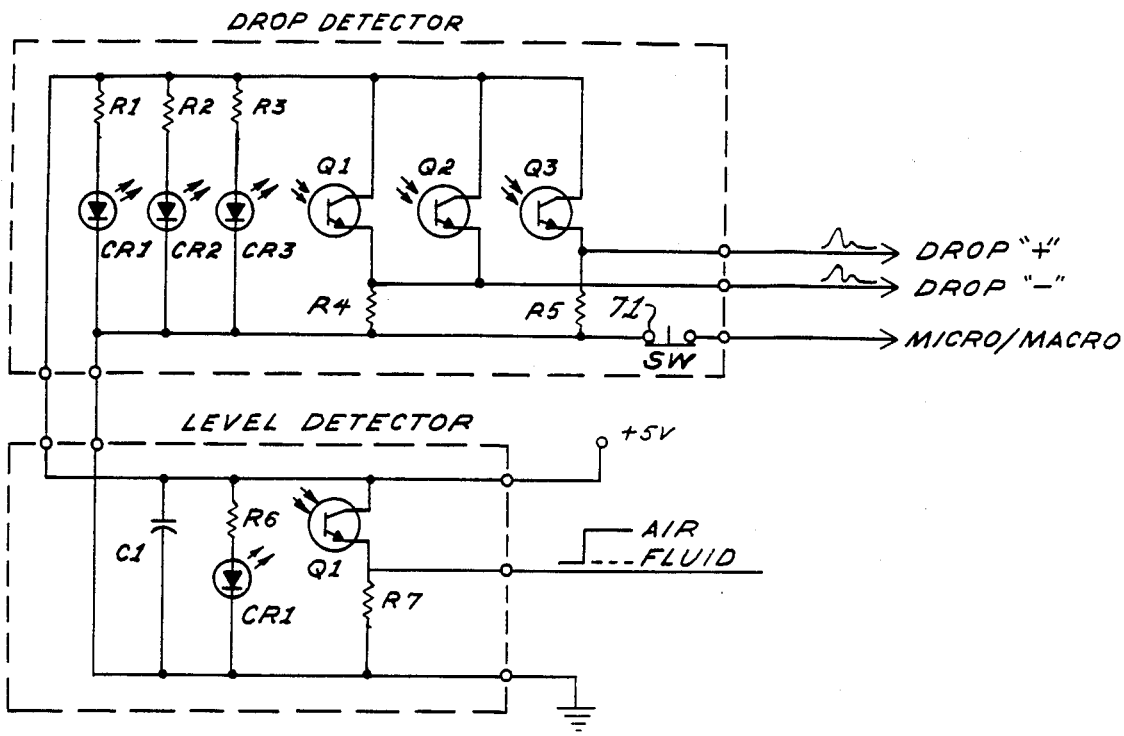
FIG. 9 is a schematic diagram of the switch, the drop detector and the level detector apparatus of FIGS. 5, 6 and 7, respectively.
Figure 10:
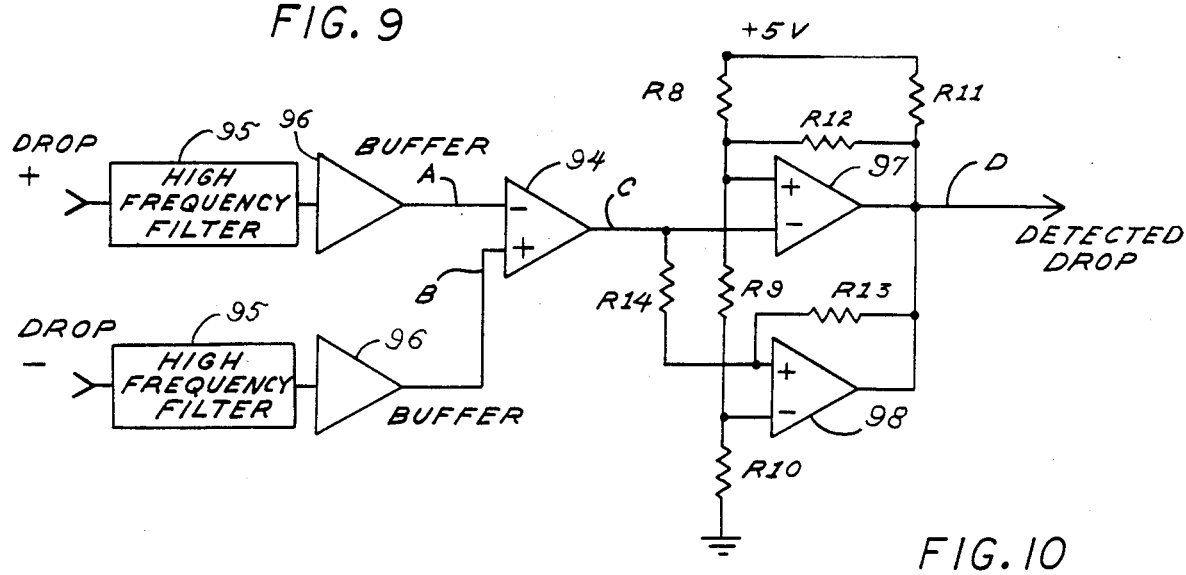
FIG. 10 is a schematic diagram of circuitry for synthesizing a drop detection signal suitable for digital processing from the signals generated by the drop detector apparatus.

Referring to FIGS. 9 and 10, the phototransistors $Q_1$ and $Q_2$ (positioned 45° apart in FIG. 6) have their emitters wired together to provide the first portion of the biphasic signal, labeled as "DROP—" in FIG. 9. The second portion of the biphasic signal is provided by phototransistor $Q_3$ which supplied a signal at its emitter labeled "DROP+". The phototransistors $Q_1$ –$Q_4$ for the drop and level detector apparatus are biased in their linear region by resistors R1–R7. Because the reflection, refraction and blockage of light caused by a drop are different for each detector pair, the signals "DROP—" and "DROP+" are not identical. Another signal from the drop detector apparatus is the "MICRO/MACRO" signal generated by the switch 71. From the level detector apparatus a "AIR/FLUID" signal is provided.

Figure 11:
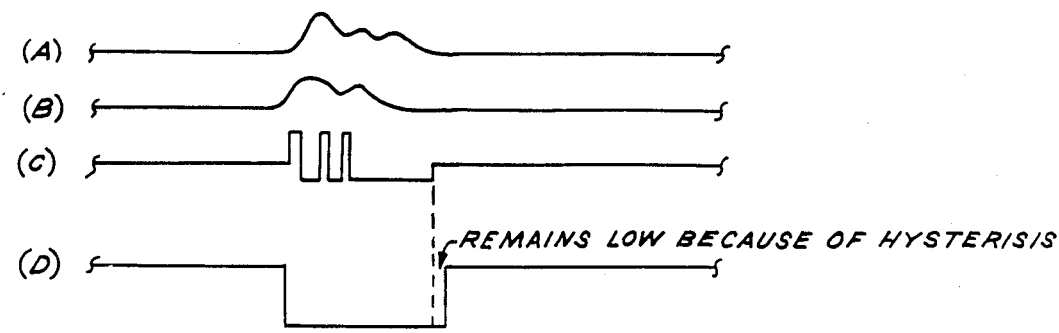
FIG. 11 is a signal timing diagram, illustrating the waveforms at locations A, B, C and D of the circuitry in FIG. 10.

From the phototransistors, the "DROP—" and "DROP+" signals are processed by the arrangement of operational amplifiers shown in FIG. 10 in order to form a drop detection signal for the microprocessor circuitry of the flow controller 19. As indicated by the signals A and B in the timing diagram of FIG. 11, the filtered and buffered signals "DROP—" and "DROP+" are somewhat different because of the different reflections, refractions and the like encountered by each pair of photodiodes and phototransistors. As a first step in processing the "DROP—" and "DROP+" signals, their relative amplitudes are compared in a differential amplifier 94 such that a single signal results which looks something like signal C illustrated in FIG. 11. Preferably, the differential amplifier 94 is biased at two volts and has a voltage range from zero to five volts.

In keeping with the invention, because the unique configuration of the sensor pairs of the drop detector apparatus creates a biphasic signal, the differential amplifier 94 sees two different signals at its inputs in response to the falling of a drop in the chamber. By providing such a biphasic signal, applicants believe the detection ability of the configuration of emitters and detectors illustrated in FIG. 6 is enhanced. Accordingly, a single signal is generated at the output of the differential amplifier which is highly indicative of a detected drop.

Each of the signals "DROP—" and "DROP+" is delivered to one of the inputs of the differential amplifier 94 by way of a high-frequency filter 95 and a buffer amplifier 96. The high-frequency (i.e., low-pass) filter 95 is intended to filter out unwanted high-frequency electromagnetic noise and the buffer amplifiers 96 are, of course, intended to isolate the phototransistors $Q_1$–$Q_3$ from the circuitry following them.

In order to provide a clean digital signal for the microprocessor circuitry which is indicative of a single drop as sensed by the sensor pairs, the multilevel signal (signal in FIG. 11) from the differential amplifier 94 is delivered to a pair of comparators 97 and 98 such that one comparator receives the signal at its positive input and the other comparator receives the signal at its negative input. The resistor ladder comprising resistors R8, R9 and R10 provides a reference voltage level for the two comparators 97 and 98 such that one of the comparators has a negative output for an input voltage level from the differential amplifier 94 which is either five or zero volts. Accordingly, with the outputs of the comparators 97 and 98 wired together, the "DETECTED DROP" signal, illustrated as signal D in FIG. 11, will remain low as long as the output of the differential amplifier 94 is active.

In order to address the possibility that the two signals A and B may momentarily have the same amplitude and thereby cause no response at the output of the differential amplifier 94, a hysterisis effect is introduced into the response of the comparators 97 and 98 by way of feedback resistors R11, R12, R13 and R14 so that the output of the comparators will not immediately return to a high voltage when a signal momentarily disappears from the output of the differential amplifier. The hysterisis also blocks low frequency glitches which may escape filtering by the high frequency filters 95.

Figure 12:
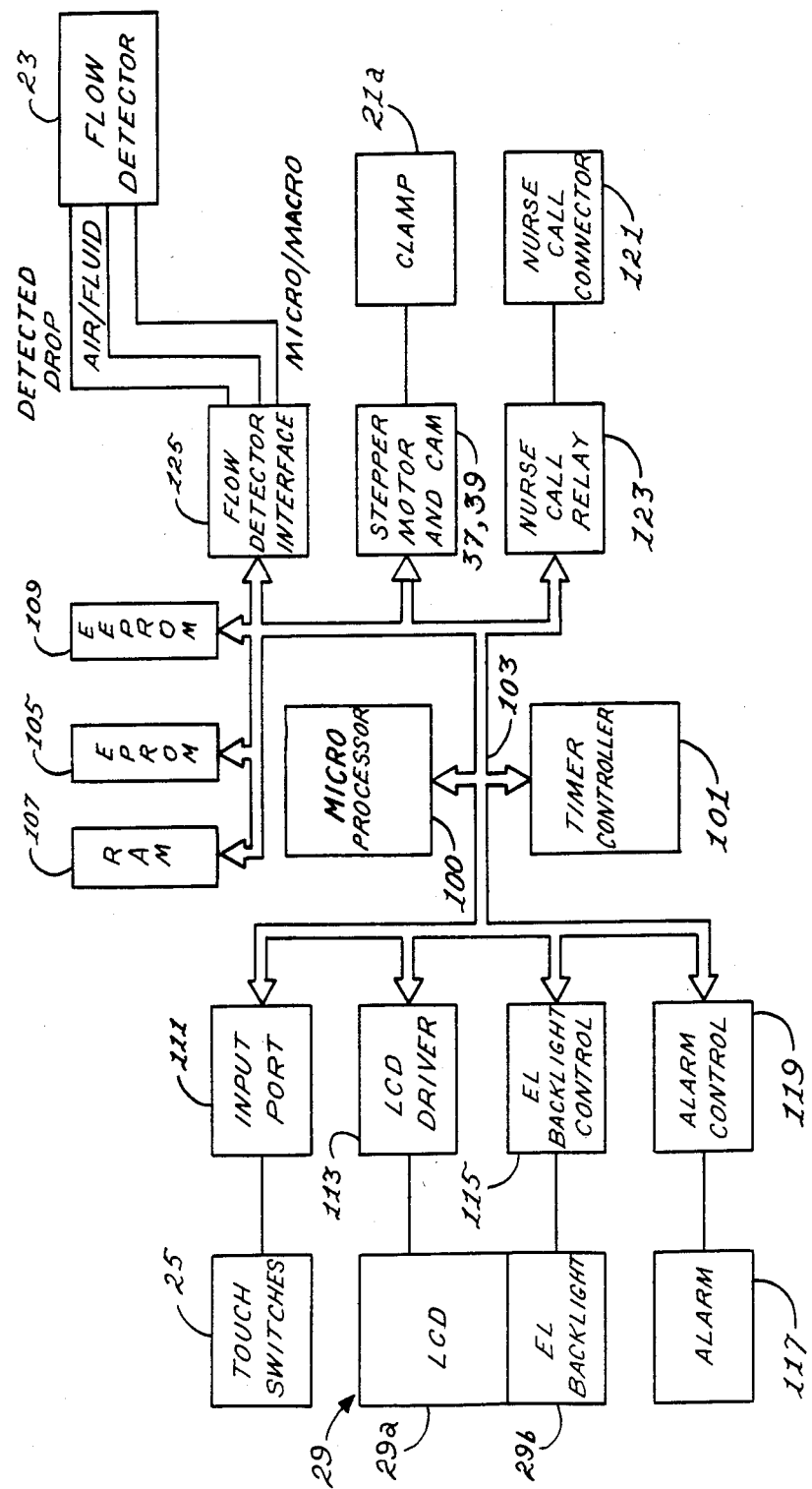
FIG. 12 is a block diagram of the microprocessor-based circuitry of the flow controller for responding to the signals from the switch, the drop detector and the level detector apparatus so as to control the resistance to fluid flow in the tubing of the administration set.

Referring to FIG. 12, the microprocessor-based circuitry of the flow controller comprises a microprocessor 100 and a timer controller 101 connected in a conventional fashion by a bi-directional bus 103. Preferably, the microprocessor 100 is a Z80 microprocessor and the timer controller 101 is a Z80L CTC; both devices are manufactured by several sources, and an example of one source is Zilog Corporation. The timer controller 101 sets priorities for software interrupts and controls program execution by the microprocessor. The program executed by the microprocessor 100 is stored in an EPROM memory 105. Additional memory space is provided by a RAM 107 and an EEPROM 109. The RAM 107 provides scratch-pad memory and the EEPROM 109 is a non-volatile memory used to store critical data so that it is not lost when all power is removed from the microprocessor circuitry. Examples of critical data which may be preserved are the identification of the last 32 alarm conditions and the identification of the last flow rate set by the user from the control panel 27.

The conventional bi-directional bus 103 includes control, data and address lines and joins the microprocessor 100 and timer controller 101 with various peripheral devices by way of conventional interfacing devices. The touchswitches 25 and display 29 on the control panel 27 of the flow controller 19 are peripherals which send and receive data to and from the microprocessor 100 by way of conventional interfaces with the bus 103 such as input port 111 for the touchswitches. The display 29 is preferably composed of a liquid crystal display 29a (LCD) and is interfaced to the microprocessor 100 by well-known LCD drivers 113. To illuminate the LCD, a conventional electroluminescent backlight (EL backlight) is used. The degree of lighting is controlled by the EL backlight control 115 in cooperation with the microprocessor 100 and timer controller 101.

In order to provide for an audible indication of a shutdown condition, an alarm peripheral 117 is included which is responsive to the microprocessor 100 by way of a conventional alarm control interface 119 connecting the alarm to the bi-directional bus line 103. In order to alert a nursing station at a remote location, a nurse call connector 121 is included which provides access to data on the bi-directional bus line 103 via a nurse call relay 123

The stepper motor 37 and cam 39 receive control signals via the bi-directional bus 103 from the microprocessor 100 in a conventional fashion. The stepper motor 37 is preferably a model A-S stepper motor manufactured by Hurst Corp., with an associated gear box 37a in FIG. 8 having a ratio of 300:1 connecting the motor to the cam 39. As explained above, the motor 37 and cam 39 cause the two arm segments 31 and 32 to cooperate and function as the clamp 21a. Finally, the flow detector 23 delivers the "DETECTED DROP", "AIR/FLUID" and "MICRO/MACRO" signals to a flow detector interface 125 which passes the data to the bi-directional bus 103.

The stepper motor 37 may be a twelve-volt motor with 100-ohms, 100-millihenries per winding, and it has a limitation of five volts on the motor 37 which prevents over stressing of the motor's gearbox 37a by limiting torque to approximately 125 inch-pounds when the pin 49 is against one of the limit stops 47a or 47b. The stepper motor 37 itself may be a two-phase unipolar drive with 48 steps-per-revolution. Preferably, the gearbox 37a has five stages and a reduction ratio of 300:1.

Figure 13C:
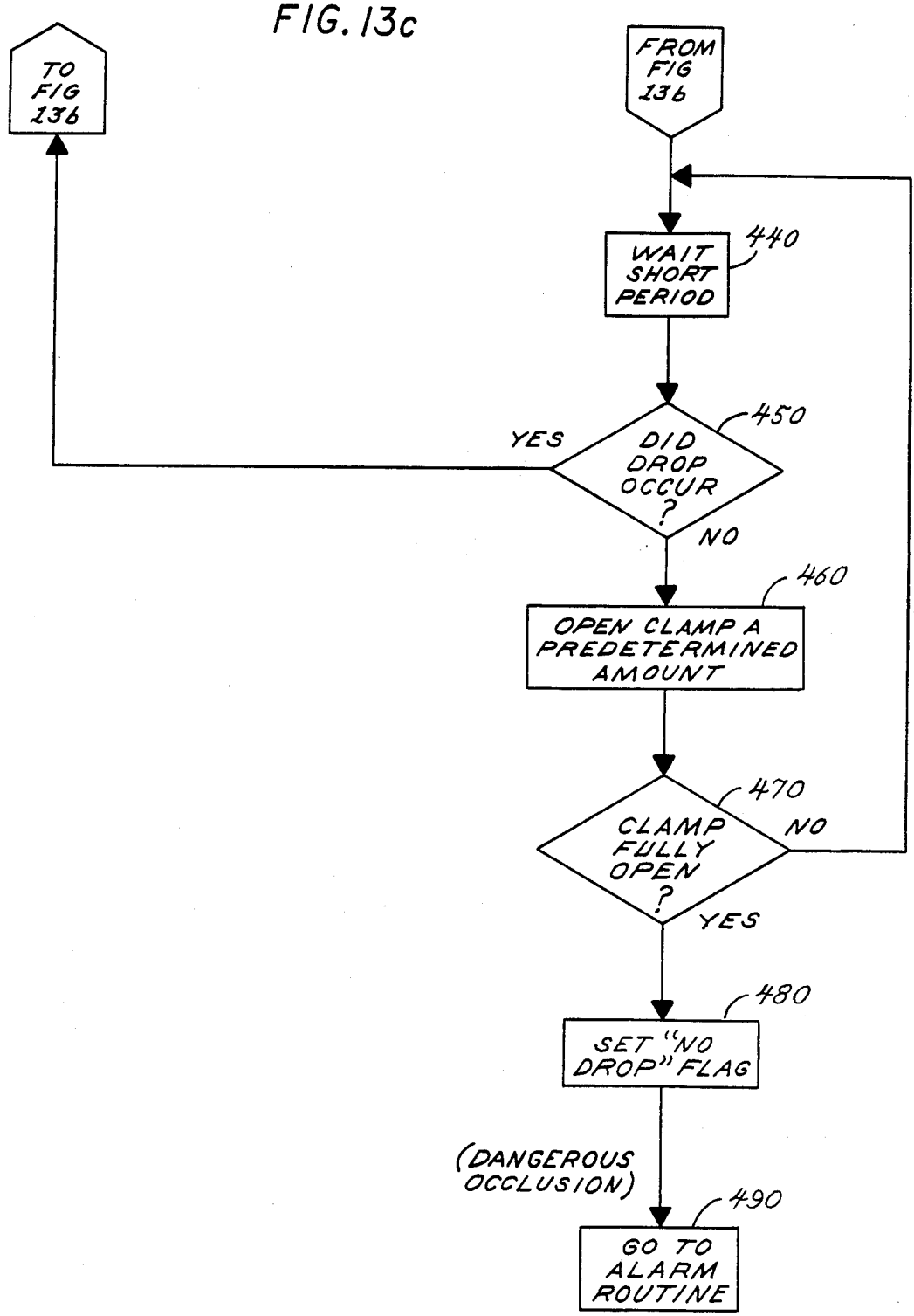
Figure 14:
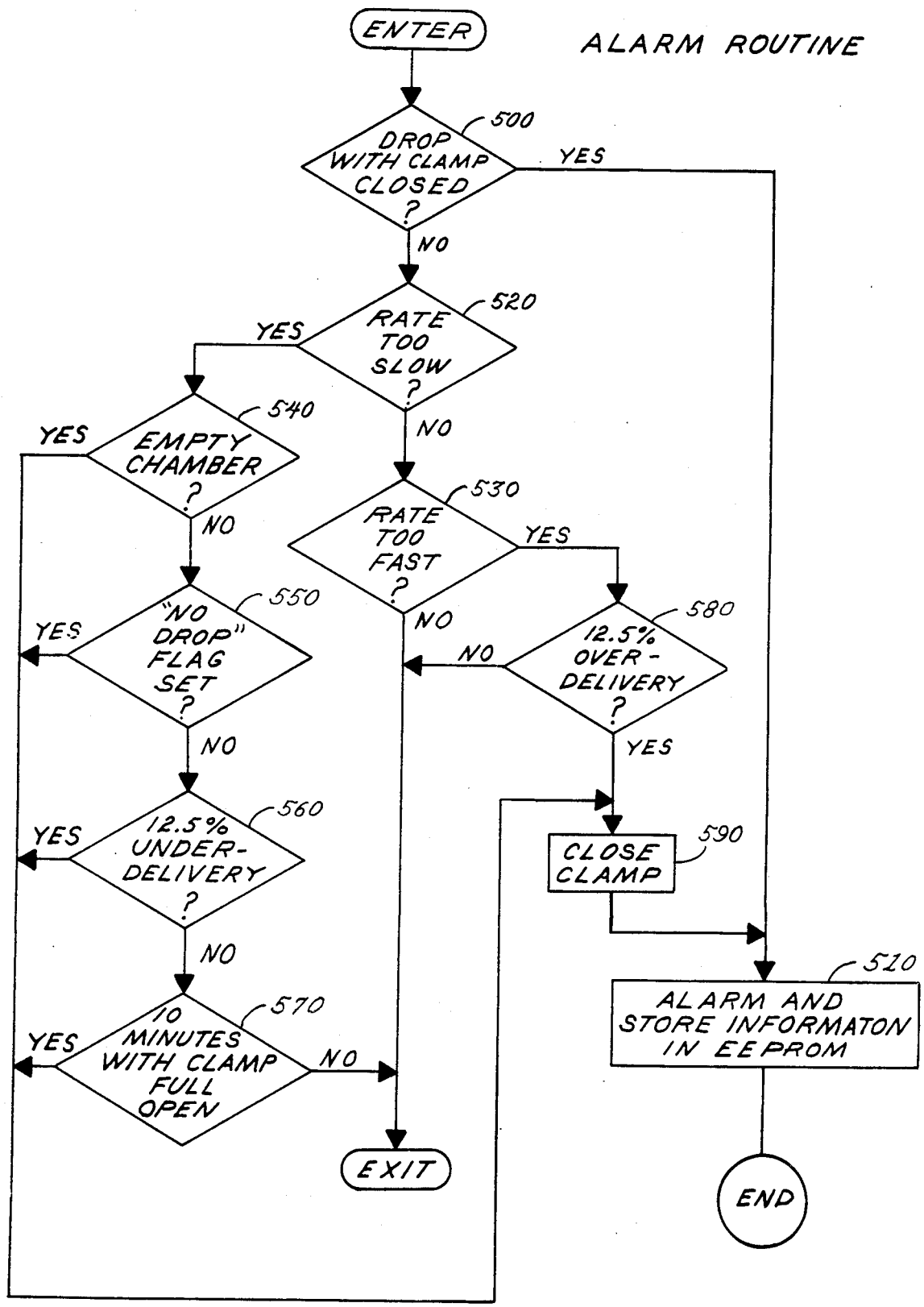
FIG. 14 is a flowchart diagram of an alarm routine for the microprocessor-based circuitry of FIG. 12 which is entered from the control routine of FIGS. 13a, 13b and 13c and which stops all fluid flow through the administration set in accordance with the invention.

The system program for execution by the microprocessor circuitry includes the steps necessary to control the position of the clamp 21a in response to both normal and abnormal flow. For normal flow, the control routine of FIGS. 13a–c commands the microprocessor circuitry to calculate a new drop interval after detection of a drop and to make any normal adjustments to the position of the clamp which may be necessary. For abnormal flow, the control routine commands the clamp 21a to perform a sequence of movements which determine the nature of the abnormal flow. During the time the control routine (FIGS. 13a–c) is waiting to execute its steps in response to the detection of a new drop, an alarm routine of FIG. 14 is executed. If an alarm condition is found to exist, the microprocessor circuitry causes the controller to shut down operation and to alert the user of an abnormal flow condition which could not be successfully corrected.

In accordance with another important aspect of the invention, the control routine includes steps which allow the flow controller to react to abnormal flow to safely shut down operation of the administration set, yet to maintain operation during abnormal flow which is not immediately dangerous and only shut down after the abnormal flow has remained uncorrected for a sufficient time period to indicate the existence of significant changes of a dangerous nature. More specifically, the flow controller aborts normal adjustment steps in response to an indication that the interval between drops is outside of a range of intervals based on the desired interval determined from the set flow rate; after normal adjustment steps are aborted, the flow controller 19 opens the clamp 21a a predetermined amount while it continues to look for a drop signal from the drop detector 23; if no drops have been detected after the clamp has been opened to a predetermined limit, the controller closes the clamp and continues to look for a drop. If a drop occurs while the clamp is closing, a streaming condition existed which has now been corrected; therefore, the controller returns to normal adjustment steps. Otherwise, when the clamp closes and still no drops are detected, the controller re-opens the clamp and looks for drops. After the clamp reaches the above-mentioned predetermined limit without the controller receiving a drop signal from the drop detector, it continues to open (but now in discrete increments) until it reaches a fully open position; at this point, if no drops have been detected, the controller closes the clamp and sounds an alarm. If at any time an empty container condition is sensed by the level detector, the controller will immediately close the clamp and sound the alarm, regardless of whether it is in the sequence of adjustment steps for normal or abnormal flow.

If no drops were detected during first closing of the clamp, then a streaming condition is very unlikely to exist. And if the AIR/FLUID signal from the level detector indicates fluid remains in the container, then the controller can safely assume an occlusion of some sort has occurred in the tubing 17. Therefore, the controller can safely execute the foregoing sequence of opening, closing, re-open and again closing the clamp—which may take approximately 45 seconds—without endangering the patient and without prematurely activating an alarm. In the course of opening, closing, re-opening and again closing the clamp, many temporary occlusions may correct themselves or it may be found that the occlusion is only partial and the initial opening of the clamp can correct it. But, if the occlusion seriously impairs fluid flow and does so for a significant time period, then the alarm will be activated. It should be noted that temporary occlusions which last as long as 60 seconds may be tolerated without compromising the potency of the infusion site.

Referring now to the particular steps of the, flowcharts, after the flow controller 19 has been turned on by pressing the ON/RESET button on the control panel 27, the hardware and software is initialized in step 150 in FIG. 13a. Thereafter, the system looks to determine if the OPERATE touchswitch has been pressed before continuing on to execute the remaining steps of the control routine. If the OPERATE touchswitch has not been pressed, the system branches to step 170 where other tasks are executed by the microprocessor circuitry which are unrelated to the invention. If it is determined in step 160 that the OPERATE touchswitch on the control panel 27 has been pressed, the system executes step 180. In keeping with the invention, in step 180 the position of the switch 71 mounted in the drop detector 23 is evaluated, and in response to the evaluation, the incremental volume amount which is added to the total volume in response to a detected drop is set in value. From step 180, the system moves to step 190 wherein the clamp 21a is driven open from a closed position until a first drop is detected.

In step 200, the system looks to determine if a drop has occurred. If no drop has occurred, the system branches to step 210 wherein the time duration since the last drop was detected is compared with a predetermined maximum time duration. This predetermined maximum time duration is dependent on the desired drop rate. Preferably, it is 150 percent of the expected drop interval for the desired drop rate. If the actual time duration is less than the maximum time duration, the system will branch to step 220 wherein the alarm routine of FIG. 14 is executed. Upon completion of the execution of the alarm routine, and assuming an alarm condition has not been found, the system returns to step 200 and again looks for another drop. The loop defined by steps 200, 210 and 220 will continue to be executed by the microprocessor circuitry until either a drop has been detected in step 200, until the maximum time interval has been exceeded in step 210 or until an alarm condition arises.

If a drop has been detected in step 200, the system branches to step 230 wherein the total volume of fluid flow stored in the RAM memory, is incremented by an amount determined from the position of the switch 71 as read by the system in step 180. In step 250, the system calculates the time interval between the occurrence of the current drop and the previous drop. Alternatively, if the time duration since the last detected drop has exceeded the maximum time duration in step 210, the system will branch to step 250 wherein the system reacts as if a drop has been detected at a drop interval equal to the maximum time duration of step 210.

After the drop interval has been calculated in step 250, the system moves to step 260 wherein the actual interval calculated in step 250 is compared to percentage values of the desired interval in order to determine if normal adjustment is appropriate or whether special steps must be executed because the interval indicates the presence of abnormal flow. Specifically, in step 260 a drop interval which is outside the range of plus or minus 50 percent of the desired interval is considered indicative of abnormal flow, and the system branches to a special set of system instructions for correction of abnormal flow.

For normal flow (i.e., for drop intervals within plus or minus 50 percent of the predicted interval), the system branches to step 270 wherein an internal counter N is zeroed (for use in the special set of instructions for abnormal flow) and normal clamp instructions are given to the stepper motor 37 in step 280, depending on the magnitude of difference between the actual drop interval and the desired drop interval and whether the interval is too long or too short. Rate correction for flow which deviates by a "normal" amount (i.e., less than plus or minus 50 percent of the desired rate) is well known and need not be discussed in further detail herein. From the normal adjustments made in step 280, the system returns to step 200 and executes the loop of steps 200, 210 and 220 as before, until a new drop is detected in step 200, a maximum time duration is exceeded in step 210 or an alarm condition has occurred.

If the measured interval between drops is outside the range of plus or minus 50 percent of the desired drop interval, the system moves from step 260 to step 290 wherein the system determines if the drop interval is too small, which indicates a flow that is too fast. If the interval is too small, the system branches to step 300 wherein the stepper motor 37 is rotated a predetermined number of steps in order to close the clamp 21a a predetermined amount. From step 300, a counter N, internal to the microprocessor 100, is initialized at step 310 and the system program returns to step 200. The counter provides a reference to determine the number of times certain steps have been consecutively executed.

If the drop interval is determined in step 290 to not be too small, it must necessarily then be too large since it is known from step 260 that the interval is not within plus or minus 50 percent of the desired interval. Accordingly, the system branches to step 320 wherein the stepper motor 37 is rotated a predetermined number of steps in a direction counter to the direction rotated in step 300 in order to open the clamp 21a a predetermined amount. In step 330, the counter N is incremented by one, and in step 340 the counter N is examined to determine whether its present count has reached a predetermined limit count. The counter N and the limit count are provided in order to allow the system to keep track of the number of consecutive times the drop interval has been found by steps 260 and 290 to be greater than 50 percent of the desired interval. If the value for the counter N is less than the limit value (preferably a value of four), the system branches back to the loop of steps 200, 210 and 220 and awaits detection of the next drop in step 200 or the expiration of the predetermined maximum time duration in step 210.

Alternatively, if the microprocessor 100 indicates that the value of the N counter has reached its predetermine limit value, the system branches to step 350 wherein the system first looks to see if a drop has occurred. If a drop has occurred, the system will again return to the loop of steps 200, 210 and 220 and await another drop or expiration of the predetermined maximum time duration. Otherwise, the system will move to step 360 wherein the position of the stepper motor 37 and the clamp 21a are memorized.

From the memorized position in step 360, the system moves to step 370 wherein the stepper motor 37 is commanded to move the clamp 21a towards its closed position. As the clamp 21a is being closed by the stepper motor 37, the program executes a loop defined by steps 380 and 390. In these steps, the system continues to look for a drop as the clamp 21a is closing. For example, when the system first executes step 380 the clamp 21a will usually not yet be closed; therefore, the next step executed is step 390 wherein the system looks to determine if a drop has occurred. If no drop has occurred, the system loops back to step 370 wherein the instruction to move the clamp 21a toward the closed position continues the movement of the clamp, and step 380 guarantees that when the clamp is closed without detection of a drop that the system will continue by executing step 400.

If a drop is detected during the execution of the loop comprising steps 370, 380 and 390, the system knows that a streaming condition has occurred and that the closing of the clamp 21a has stopped the stream and the fluid is now forming discrete drops. Because the streaming has been stopped as indicated by a detection of a drop, the system is returned via step 410, which zeros the counter N, to step 230 where the total volume is incremented and the drop interval is calculated for another determination in steps 260 and 290 of whether the flow is normal or abnormal.

Referring to step 400, if the clamp 21a has reached a fully closed position without detection of a drop, the system instructs the stepper motor 37 to rotate in an opposite direction in order to begin opening the clamp. As the clamp 21a is opened, the system looks in step 420 to determine whether the present position of the clamp is equal to the position memorized in step 360. If the clamp 21a has not yet been opened to its previously memorized position, the system branches from step 420 to step 430 wherein a determination is made whether a drop has occurred. If no drop has occurred, then the system returns to step 400 and continues to move the clamp open. Otherwise, the detection of a drop in step 420 will cause the system to leave the loop formed by steps 400, 410 and 420 and return via step 410 to step 230.

If in step 420, the clamp 21a has been opened to its memorized position without a detection of a drop signal, the system waits for a short period (preferably approximately one second) in step 440 before proceeding to step 450 wherein the system again looks to see if a drop has occurred. If a drop has not occurred during the short period in step 440, the program branches from step 450 to step 460. Otherwise, if a drop has occurred, the program returns to step 230 via step 410 as it did in response to detection of drops in steps 390 and 430.

If no drop has been detected in step 450, the microprocessor circuitry commands the stepper motor 37 to open the clamp 21a a predetermined amount in step 460. If the clamp 21a is not found to be fully open in step 470, the system loops back to step 440 and again executes the loop comprising steps 440, 450, 460 and 470. The system continues in this loop until the clamp is fully open. Preferably, the clamp 21a is considered to be fully open when the offset cam 39 has been rotated so that the cam extension pin 49 is contacting the limit stop 47b. When the clamp 21a has reached its fully open position, the system branches to 480 wherein a "no drop" flag is set within the microprocessor circuitry. The setting of the "no drop" flag indicates to the alarm routine that a dangerous occlusion has occurred since the system has been unable to re-initiate flow and has had a condition of no flow for a significant amount of time (the time to execute the commands from step 360 to step 480—approximately 45 seconds), and therefore a dangerously long condition of no flow or occlusion has occurred. Accordingly, the system branches to the alarm routine of FIG. 14 at step 490 wherein the clamp 21a is closed, and the system is shut down.

Turning to the steps of the alarm routine illustrated in FIG. 14, this routine is executed between detection of drops in the loop of steps 200, 210 and 220 in the control routine. Also, the alarm routine is entered from step 490 of the control routine when abnormal flow is detected which cannot be corrected within a reasonable time period. In step 500 of the alarm routine, the system first looks to determine if a drop has been detected with the clamp 21a in its closed position. Because no flow should occur with the clamp 21a in its closed position, the detection of a drop with the clamp closed indicates a system fault. Therefore, the system will branch to step 510 wherein the alarm 117 (FIG. 12) is activated and an alarm code is stored in the EEPROM 109 in order that the user may later interrogate the memory to determine the cause of the system shutdown.

From step 510 the systems shuts down and further control of the flow is stopped until the user reinitializes the system by sequentially pressing the ON/RESET and the OPERATE buttons. Of course, the user must correct the cause of the system shutdown before re-initializing the system and re-starting operation since an uncorrected administration set would only result in another system shutdown.

If the system determines in step 500 that there has not been a drop detected with the clamp closed, the system moves to steps 520 and 530 to determine if the rate is too slow or too fast. If the system is operating normally and the actual rate is within a predetermined range of the desired rate such that correction of the flow rate by rotation of the stepper motor 37 is unnecessary, then the alarm routine will exit back to the control program of step 200. Otherwise, the program will either execute steps 540, 550, 560 and 570 if the rate is too slow as determined in step 520. Or, the step 580 will be executed if the rate is determined to be too fast in step 530.

Looking first at the situation where the rate is too slow, the system will branch from step 520 to step 540 wherein the signal level of the air/fluid line from the level detector circuitry of the flow detector 23 is examined in order to determine if the fluid level in the bottom of the drop chamber 18 is at a level which indicates the container 13 has fluid remaining in it. If the air/fluid signal indicates that the fluid level in the drop chamber 18 is low, the system will branch to step 590 wherein the clamp 21a is closed by the stepper motor 37, and the alarm 117 is activated in step 510; also, a code indicative of the nature of the system fault (i.e., an empty drop chamber) is recorded in the EEPROM 109.

If the fluid level in the pool gathered at the bottom of the drop chamber 18 is not below the level sensed by the level detector, then the system branches to step 550 wherein the status of the "no drop" flag is checked. If the alarm routine is being entered from step 490 in the control routine, then the "no drop" flag is set and therefore the system will branch to steps 590 and 510 to close the clamp 21a and activate the alarm 117.

If neither an empty drop chamber 18 nor a "no drop" flag is detected, then the system moves to step 560 wherein a determination is made whether the total volume of fluid delivered is greater than a predetermined percentage of the total volume which should be delivered at the current time, assuming the desired flow rate. In the illustrated embodiment, the predetermined percentage is 12.5 percent under-delivery. That is, if the volume of fluid delivered to the patient falls below 87.5 percent of the desired volume to be given the patient, then the system will branch to steps 590 and 510 in order to shutdown the system since such an under-delivery of fluid indicates that the system has been unable to maintain an adequate flow rate.

In step 570, the system looks to determine if 10 minutes (cumulative) has elapsed with the clamp 21a in its fully open position (i.e., with the stepper motor 37 rotated to be biased against its stop 47b). If the flow controller 19 is operating with the clamp 21a in its fully open position and has been operating this way for 10 minutes and yet the rate is too slow, then the system assumes that something is wrong and branches to steps 590 and 510 in order to shutdown the system and alarm the user. Finally, if the rate is too slow but none of the conditions in steps 540, 550, 560 and 570 exist, then the system will exit the alarm routine and return to the control routine at step 200.

If the flow rate is determined to be too fast in step 530, the system branches to step 580 wherein a determination is made whether a percentage overdelivery of fluid volume has occurred. Specifically, if the administration set has delivered 112.5 percent of the desired volume at the time of execution of step 580, then the system will again execute steps 590 and 510 to shutdown the administration set and alarm the operator. Otherwise, the system will exit the alarm routine and return to step 200 of the control routine.

It will be appreciated from the foregoing that a flow controller according to the invention provides increased reliability in performing the task of controlling the flow rate and volume of fluid administered to a patient by a gravity-feed administration set. Unlike previous flow controllers, the flow controller of the invention provides for effective response to dangerous abnormal flow conditions such as streaming without causing the system to respond prematurely to other types of abnormal flow which are not nearly as dangerous to the patient over a reasonably short period of time. Accordingly, the flow controller of the invention is tolerant of temporary occlusions, and therefore it is much more flexible in responding to changes in flow which may be caused merely by the movement of the patient or other types of dynamic changes which are common yet which do not give rise to conditions which are immediately dangerous to the patient. Therefore, partial occlusions caused by patient movement will not trigger a "false alarm" by the system, but instead the system will tolerate the partial occlusion until the accumulative effect of the partial occlusion becomes potentially dangerous to the patient.

We claim:

1. A system for controlling the resistance to fluid flow in an administration set which includes a drop chamber, said system comprising in combination:
   a drop detector for sensing drops of fluid falling in said chamber;
   a controller responsive to said drop detector for determining the actual flow rate of fluid in said administration set and comparing said actual flow rate with a predetermined desired flow rate;
   clamping means responsive to said controller for opening or closing a clamp pinching the tubing of said administration set, thereby adjusting the resistance to fluid flow in said administration set; and
   said controller including (1) first means for determining if the interval between successive drops is greater than a given percentage of the drop interval associated with said predetermined desired flow rate, (2) second means responsive to said first means to sequentially command said clamping means to open said clamp a predetermined amount, fully close said clamp, reopen said clamp and again close said clamp, and (3) third means for aborting the sequential movement of said clamp initiated by said second means if a drop is detected by said drop detector.

2. A system as set forth in claim 1 wherein said controller includes an alarm responsive to the completion of the sequential movement of said clamp by said second means.

3. A system as set forth in claim 1 including:
   a level detector associated with said drop detector for sensing a reservoir of fluid in the bottom of said drop chamber;
   fourth means in said controller responsive to an indication from said level detector of a low level of fluid in said reservoir of fluid; and
   said clamping means responsive to said fourth means to close said clamp.

4. A system as set forth in claim 1 wherein said controller includes:
   a fifth means for determining if the total volume of fluid actually delivered is outside a predetermined range of volumes determined by the expected total volume of fluid at the predetermined rate; and
   said clamping means responsive to said fifth means for closing said clamp when the total volume of fluid actually delivered is outside said predetermined range of volumes determined by said expected total volume of fluid.

5. A system as set forth in claim 1 including:
   a drop orifice in said drop chamber;
   indicia associated with said drop chamber for indicating the size of the orifice in said drop chamber;
   sensing means physically associated with said drop detector for sensing said indicia when said drop detector is joined to said drop chamber; and
   said controller including a sixth means for determining a parameter of the fluid flow through said administration set.

6. A system as set forth in claim 5 wherein said sixth means increments a total volume value stored in a memory of said controller in response to the detection of a falling drop by said drop detector, wherein the incremental amount is determined by the indicia sensed by said sensing means.

7. A system as set forth in claim 5 wherein said sensing means is a switch mounted to said drop detector and includes a spring-loaded pin biased to protrude from the surface of said drop detector when said switch is in a first state; and
   said drop chamber including a shoulder portion which has (a) a solid area for depressing said pin and placing said switch into a second state if the drop chamber is characterized by drops of a first size or (b) a holed area for receiving said pin such that said switch remains in said first state if said drop chamber is characterized by drops of a second size.

8. A system as set forth in claim 1 wherein said drop detector comprises:
   a housing having a bore for receiving said drop detector;
   a plurality of pairs of radiation emitters and detectors mounted to a first substrate within said housing and each pair providing an optical link spanning said bore such that all of the optical links are substantially coplanar to a reference plane wherein said reference plane is approximately orthogonal to the longitudinal axis of said drop chamber when said drop chamber is received by said bore of said housing;

a first one of said pairs of emitters and detectors positioned with respect to a second one of said pairs such that the optical links of the first and second pairs intersect in an area of the bore and are approximately perpendicular to one another;

a third one of said pairs of emitters and detectors positioned with respect to said first and second ones of said pairs such that the optical link of said third pair intersects each of the optical links of said first and second pairs at an angle of approximately 45 degrees as measured from the point of intersection; and whereby drops falling in said drop detector may be detected when the longitudinal axis of said drop chamber is tilted from a vertical reference axis by an angle of inclination approaching 30 degrees.

9. A system as set forth in claim 8 including a level detector in the housing for said drop detector which detects the level of fluid pooled at the bottom of said drop chamber;

fourth means in said controller responsive to an indication from said level detector of a low level of fluid pooled at the bottom of said drop chamber; and said clamping means responsive to said fourth means to close said clamp.

10. A system as set forth in claim 9 wherein said level detector comprises a radiation emitter and detector mounted to a second substrate within the housing of said drop detector such that the optical link between the emitter and detector is intercepted by the pooled fluid of said drop chamber when the chamber is received by said bore in said housing.

11. A system as set forth in claim 1 wherein said drop detector comprises:

a housing having a bore for receiving said drop detector;

a plurality of pairs of radiation emitters and detectors mounted to a first substrate within said housing and each pair providing an optical link spanning said bore such that falling drops in said drop chamber cut said optical links when said drop chamber is positioned in said bore;

seventh means responsive to said plurality of radiation emitters and detectors for providing a plurality of analog signals; and eighth means responsive to said seventh means for comparing said plurality of analog signals with one another and thereby providing a single signal indicative of a detected drop.

12. In a system for controlling the resistance to fluid in an administration set by maneuvering a clamp to pinch the tubing of said set, a method for correcting for over or under delivery of fluid caused by abnormal flow comprising the steps of:

sensing a rate of falling drops in said drop chamber which is less than a predetermined rate;

aborting normal adjustment steps;

opening said clamp until a drop is sensed or until the clamp reaches a first predetermined open position;

closing said clamp if said clamp reaches said first predetermined open position without detection of a drop;

reopening said clamp and continuing to look for a falling drop if said clamp reaches a fully closed position wherein fluid flow is completely pinched off without detection of a falling drop;

immediately closing clamp to cut off fluid flow if said clamp reaches a second predetermined open position without detection of a falling drop, and sounding an alarm.

13. A method as set forth in claim 12, including the steps of:

sensing the presence of a pool of fluid in the bottom of said drop chamber; and immediately closing said clamp if said pool of fluid falls below a predetermined level.

14. A method as set forth in claim 12 wherein normal adjustment steps are re-instituted after a drop has been detected during opening or closing of said clamp.

15. In a system for (a) delivering fluid to a patient by way of an administraation set having a drop chamber, (b) detecting the falling of drops in said drop chamber and (c) controlling the rate of fluid volume delivered to the patient in response to the rate of falling drops, an apparatus for automatically compensating for changes in the size of the falling drops comprising in combination:

first means for detecting falling drops in said chamber;

a drop orifice in said drop chamber;

indicia associated with said drop chamber for indicating the size of the orifice in said drop chamber;

second means physically associated with said first means for sensing said indicia; and third means responsive to said first and second means for determining a parameter of the flow of fluid through said administration set.

16. An apparatus as set forth in claim 15 including:

a memory for storing the total volume of fluid delivered by the administration set; and said third means incrementing the value of the total volume stored in said memory in response to the detection of a falling drop by said first means and by an incremented amount determined by the indicia sensed by said second means.

17. An apparatus as set forth in claim 15 including:

a housing for said first means including a bore for receiving said drop chamber;

said second means including a switch mounted to said housing and having a spring-loaded pin associated therewith which biases the switch in a first state such that the pin protrudes from the surface of said housing in an area which is intended to receive a shoulder of said drop chamber; and a shoulder portion of said drop chamber having (1) a solid area for depressing said pin and placing said switch into a second state if said drop chamber is characterized by drops of a first size or (2) a holed area for receiving said pin such that said switch remains in said first state if said drop chamber is characterized by drops of a second size.

18. An apparatus as set forth in claim 15 wherein said first means comprises:

a housing having a bore for receiving said drop chamber;

a plurality of pairs of radiation emitters and detectors mounted to a first substrate within said housing and each pair providing an optical link spanning said bore such that all of the optical links are substantially coplanar to a reference plane wherein said reference plane is approximately orthogonal to the longitudinal axis of said drop chamber when said drop chamber is received by said bore of said housing; and said plurality of pairs of radiation emitters and detectors positioned on said first substrate such that their optical links intersect one another in an area of said bore in a manner which provides for reliable detection of falling drops when the longitudinal axis of said drop chamber is tilted from a vertical reference axis by an angle of inclination approaching 30 degrees.

19. In a system for provided a controlled flow of fluid through an administration set, the combination comprising:

a drop chamber having indicia which is indicative of the size of the drops formed in said chamber;

a drop detector for detecting falling drops in said drop chamber and having a receptacle for receiving the drop chamber;

sensing means associated with said drop detector for sensing said indicia when said drop chamber is received by the receptacle of said drop detector; and control means responsive to said drop detector and said sensing means for determining a parameter of the flow of fluid through said administration set.

20. The combination as set forth in claim 19 including:

a memory for storing the total volume of fluid delivered by the administration set; and said control means incrementing the value of the total volume stored in said memory in response to the detection of a falling drop by said drop detector and by an incremented amount determined by the indicia sensed by said sensing means.

21. The combination as set forth in claim 20 wherein said control means is also responsive to said drop detector for determining the actual flow rate of fluid in said administration set and comparing said actual flow rate with a predetermined flow rate stored in said memory;

clamping means responsive to said control means for opening or closing a clamp for variably pinching the tubing of said administration set, thereby adjusting the resistance to fluid flow in said administration set; and said control means including (a) first means for determining if said actual flow rate is less than a given percentage of said predetermined flow rate, (b) second means responsive to said first means to sequentially command said clamping means to open said clamp, close said clamp, reopen said clamp and again close said clamp, and (c) third means for aborting said sequential movement of said clamp by said second means if a drop is detected by said drop detector during execution of said sequence.

22. A drop detector of a flow controller for detecting drops of fluid falling in a drop chamber of an administration set, said drop detector comprising:

a plurality of pairs of radiation emitters and detectors mounted to a first substrate within said drop detector and each pair providing an optical link spanning a bore in said drop detector such that all the optical links are coplanar to a reference plane wherein said reference plane is approximately orthogonal to the longitudinal axis of said drop chamber when said drop chamber is received by said bore in said drop detector;

a first one of said pairs of radiation emitters and detectors positioned with respect to a second one of said pairs such that the optical links of the first and second pairs intersect in an area of the bore and are approximately perpendicular to one another;

a third one of said pairs of radiation emitters and detectors positioned with respect to said first and second ones of said pairs such that the optical link of said third pair intersects each of the optical links of said first and second pairs at an angle of approximately 45 degrees as measured from the point of intersection; and whereby drops falling in said drop detector may be detected when the longitudinal axis of said drop chamber is tilted from a vertical reference axis by an angle of inclination approaching 30 degrees.

23. A drop detector as set forth in claim 22 including:

first means responsive to said plurality of radiation emitters and detectors for providing a plurality of analog signals; and second means responsive to said first means for comparing said plurality of analog signals with one another and thereby providing a single signal indicative of a detected drop.

24. A drop detector of a flow controller for detecting drops of fluid falling in a drop chamber of an administration set, said drop detector comprising:

a housing having a bore for receiving said drop detector;

a plurality of pairs of radiation emitters and detectors mounted to a first substrate within said housing and each pair providing an optical link spanning said bore such that falling drops in said drop chamber cut said optical links when said drop chamber is positioned in said bore;

first means responsive to said plurality of radiation emitters and detectors for providing a plurality of analog signals; and second means responsive to said first means for comparing said plurality of analog signals with one another and thereby providing a single signal indicative of a detected drop.

25. A drop detector as set forth in claim 24 wherein said optical links are substantially coplanar to a reference plane wherein said reference plane is approximately orthogonal to the longitudinal axis of said drop chamber when said drop chamber is received by said bore of said housing;

a first one of said pairs of emitters and detectors positioned with respect to a second one of said pairs such that the optical links of the first and second pairs intersect in an area of the bore and are approximately perpendicular to one another;

a third one of said pairs of emitters and detectors positioned with respect to said first and second ones of said pairs such that the optical link of said third pair intersects each of the optical links of said first and second pairs at an angle of approximately 45 degrees as measured from the point of intersection; and whereby drops falling in said drop detector may be detected when the longitudinal axis of said drop chamber is tilted from a vertical reference axis by an angle of inclination approaching 30 degrees.

* * * * *